(12) United States Patent
Defreitas et al.

(10) Patent No.: US 11,364,000 B2
(45) Date of Patent: Jun. 21, 2022

(54) SYSTEMS AND METHODS FOR PIVOTING COMPRESSION PADDLES

(71) Applicant: HOLOGIC, INC., Marlborough, MA (US)

(72) Inventors: Kenneth F. Defreitas, Marlborough, MA (US); Thomas Deyoung, Marlborough, MA (US); Jeffrey Harold Paige, Marlborough, MA (US); Alan Rego, Marlborough, MA (US); Baorui Ren, Marlborough, MA (US); Jay A. Stein, Marlborough, MA (US); David Wolff, Marlborough, MA (US)

(73) Assignee: Hologic, Inc., Marlborough, MA (US)

( * ) Notice: Subject to any disclaimer, the term of this patent is extended or adjusted under 35 U.S.C. 154(b) by 0 days.

(21) Appl. No.: 16/981,950

(22) PCT Filed: May 24, 2019

(86) PCT No.: PCT/US2019/034010
§ 371 (c)(1),
(2) Date: Sep. 17, 2020

(87) PCT Pub. No.: WO2019/227051
PCT Pub. Date: Nov. 28, 2019

(65) Prior Publication Data
US 2021/0030375 A1  Feb. 4, 2021

Related U.S. Application Data

(60) Provisional application No. 62/814,041, filed on Mar. 5, 2019, provisional application No. 62/732,771, filed
(Continued)

(51) Int. Cl.
*A61B 6/00* (2006.01)
*A61B 6/04* (2006.01)
(Continued)

(52) U.S. Cl.
CPC .......... *A61B 6/0414* (2013.01); *A61B 6/0435* (2013.01); *A61B 6/502* (2013.01); *A61B 6/025* (2013.01); *A61B 6/032* (2013.01)

(58) Field of Classification Search
CPC ..... A61B 6/502; A61B 6/0435; A61B 6/0414; A61B 17/00491; A61B 6/0421; A61B 6/04; A61B 6/0407
See application file for complete search history.

(56) References Cited

U.S. PATENT DOCUMENTS

| 4,744,099 A | 5/1988 | Huettenrauch et al. |
| 5,506,877 A | 4/1996 | Niklason et al. |
| (Continued) | | |

FOREIGN PATENT DOCUMENTS

JP   2011-206436 A   10/2011

OTHER PUBLICATIONS

International Search Report and Written Opinion of the International Searching Authority for International Patent Application No. PCT/US2019/034010 dated Jul. 7, 2020, 18 pages.

*Primary Examiner* — Don K Wong
(74) *Attorney, Agent, or Firm* — Merchant & Gould P.C.

(57) ABSTRACT

The housing for a breast imaging system contains an x-ray source and is configured to rotate relative to the breast. The housing for an x-ray receptor has a breast support platform and extends from an arm assembly which rotates independently from the x-ray source housing. A compression arm assembly connected to the arm assembly moves between a first linear position proximate the x-ray receptor housing and a second linear position distal the x-ray receptor housing. A
(Continued)

pair of extension arms are pivotably connected to a strut which removably secures a compression paddle to the compression arm assembly substrate. The extension arms move between a first pivoted position substantially aligned with the strut and a second pivoted position disposed at an angle to the strut.

20 Claims, 14 Drawing Sheets

Related U.S. Application Data on Sep. 18, 2018, provisional application No. 62/676,609, filed on May 25, 2018.

(51) Int. Cl.
*A61B 6/02* (2006.01)
*A61B 6/03* (2006.01)

(56) References Cited

U.S. PATENT DOCUMENTS

| | | |
|---|---|---|
| 6,577,702 B1 | 6/2003 | Lebovic |
| 8,401,145 B1 | 3/2013 | Boutte |
| 2003/0007597 A1 | 1/2003 | Higgins |
| 2004/0218727 A1 | 11/2004 | Shoenfeld |
| 2005/0008117 A1 | 1/2005 | Livingston |
| 2006/0050844 A1 | 3/2006 | Galkin |
| 2006/0126794 A1 | 6/2006 | Hermann |
| 2007/0280412 A1 | 12/2007 | Defreitas et al. |
| 2010/0067659 A1 | 3/2010 | Bush |
| 2010/0179604 A1 | 7/2010 | Campagna |
| 2012/0114096 A1 | 5/2012 | Lebovic et al. |
| 2013/0129039 A1 | 5/2013 | DeFreitas |
| 2014/0177791 A1 | 6/2014 | Otokuni et al. |
| 2015/0305693 A1 | 10/2015 | Galambos |
| 2016/0081633 A1 | 3/2016 | Stango |
| 2016/0183898 A1* | 6/2016 | Cormican ............. A61B 6/502 378/37 |
| 2016/0206229 A1 | 7/2016 | Arai et al. |
| 2017/0340303 A1 | 11/2017 | Stango et al. |

* cited by examiner

SYSTEMS AND METHODS FOR PIVOTING COMPRESSION PADDLES

CROSS-REFERENCE TO RELATED APPLICATIONS

This application is a National Stage Application of PCT/US2019/034010, filed on May 24, 2019, which claims the benefit of priority to U.S. Provisional Application No. 62/676,609, filed May 25, 2018, U.S. Provisional Application No. 62/732,771, filed Sep. 18, 2018, and U.S. Provisional Application No. 62/814,041, filed Mar. 5, 2019, which applications are hereby incorporated in their entireties by reference. To the extent appropriate, a claim of priority is made to each of the above disclosed applications.

BACKGROUND

Compression during mammography and tomosynthesis imaging serves a number of purposes. For example, it: (1) makes the breast thinner in the direction of x-ray flux and thereby reduces patient radiation exposure from the level required to image the thicker parts of a breast that are not compressed; (2) makes the breast more uniform in thickness in the direction of x-ray flux and thereby facilitates more uniform exposure at the image plane over the entire breast image; (3) immobilizes the breast during the x-ray exposure and thereby reduces image blurring; and (4) brings breast tissues out from the chest wall into the imaging exposure field and thus allows for more tissue imaging. As the breast is being compressed, typically a technologist manipulates the breast to position it appropriately and counter the tendency that compression has of pushing breast tissue toward the chest wall and out of the image field.

Standard compression methods for mammography and tomosynthesis use a movable, rigid, radiolucent compression paddle. The breast is placed on a breast support platform that typically is flat, and the paddle then compresses the breast, usually while a technologist or other health professional is holding the breast in place. The technologist may also manipulate the breast to ensure proper tissue coverage in the image receptor's field of view.

One known challenge in mammography and breast tomosynthesis is the discomfort the patient may feel when the breast is compressed, which must be done with sufficient force to immobilize the breast and spread out the breast tissues for x-ray imaging. Discomfort may potentially cause the patient to move, which negatively impacts image quality. Discomfort may also potentially dissuade patients from getting screened for breast cancer. Another known challenge is to ensure that the imaged field includes the desired amount of breast tissue.

SUMMARY

In one aspect, the technology relates to an imaging system for imaging breast, the system having: an x-ray source housing configured to rotate relative the breast; an x-ray source disposed within the x-ray source housing; an arm assembly rotatable independent of the x-ray source housing; an x-ray receptor housing extending from the arm assembly, wherein the x-ray receptor housing includes a breast support platform; an x-ray receptor disposed within the x-ray receptor housing; a compression arm assembly movably connected to the arm assembly substantially between the x-ray source housing and the x-ray receptor housing, wherein the compression arm assembly is movable between a first linear position proximate the x-ray receptor housing and a second linear position distal the x-ray receptor housing; a compression paddle having: a strut for removably securing the compression paddle to the compression arm assembly; a substrate; and a pair of extension arms extending from the substrate, wherein the pair of extension arms are pivotably connected to the strut between a first pivoted position where the pair of extension arms are substantially aligned with the strut and a second pivoted position where the pair of extension arms are disposed at an angle to the strut. In an example, the pair of extension arms define therebetween a clearance gap, and wherein when in the first pivoted position, the strut is disposed in the clearance gap, and wherein when in the second pivoted position, the compression arm is disposed in the clearance gap. In another example, the angle has a substantially orthogonal angle. In yet another example, the imaging system further includes a foam secured to the substrate. In still another example, the imaging system further includes at least one system control for controlling a pivoting movement of the compression paddle and a linear movement of the compression arm.

In another aspect, the technology relates to a method of imaging a breast with an imagining system having a support platform disposed in a substantially horizontal orientation, a compression arm linearly positionable relative to the support platform, and a compression paddle pivotably positionable relative to the compression arm, the method including: disposing the imaging system in a procedure-ready condition, wherein in the procedure-ready condition, the compression paddle in is a substantially vertical orientation and the compression arm is disposed at a first height above the support platform; moving the imaging system to a compression-ready condition, wherein in the compression-ready condition, the compression paddle in is a substantially horizontal orientation and the compression arm is disposed at a second height above the support platform, wherein the second height is greater than the first height; and moving the imaging system to a compressed condition, wherein in the compressed condition, the compression paddle in is a substantially horizontal orientation and the compression arm is disposed at a third height above the support platform. In an example, the third height is less than the first height. In another example, during movement to the compression-ready condition, a pivotal movement of the compression paddle is performed substantially simultaneously with a linear movement of the compression arm. In yet another example, during movement to the compressed condition, only linear movement of the compression arm is performed. In still another example, the method further includes imaging the breast when the imaging system is in the compressed condition.

DETAILED DESCRIPTION

Figure 1A:
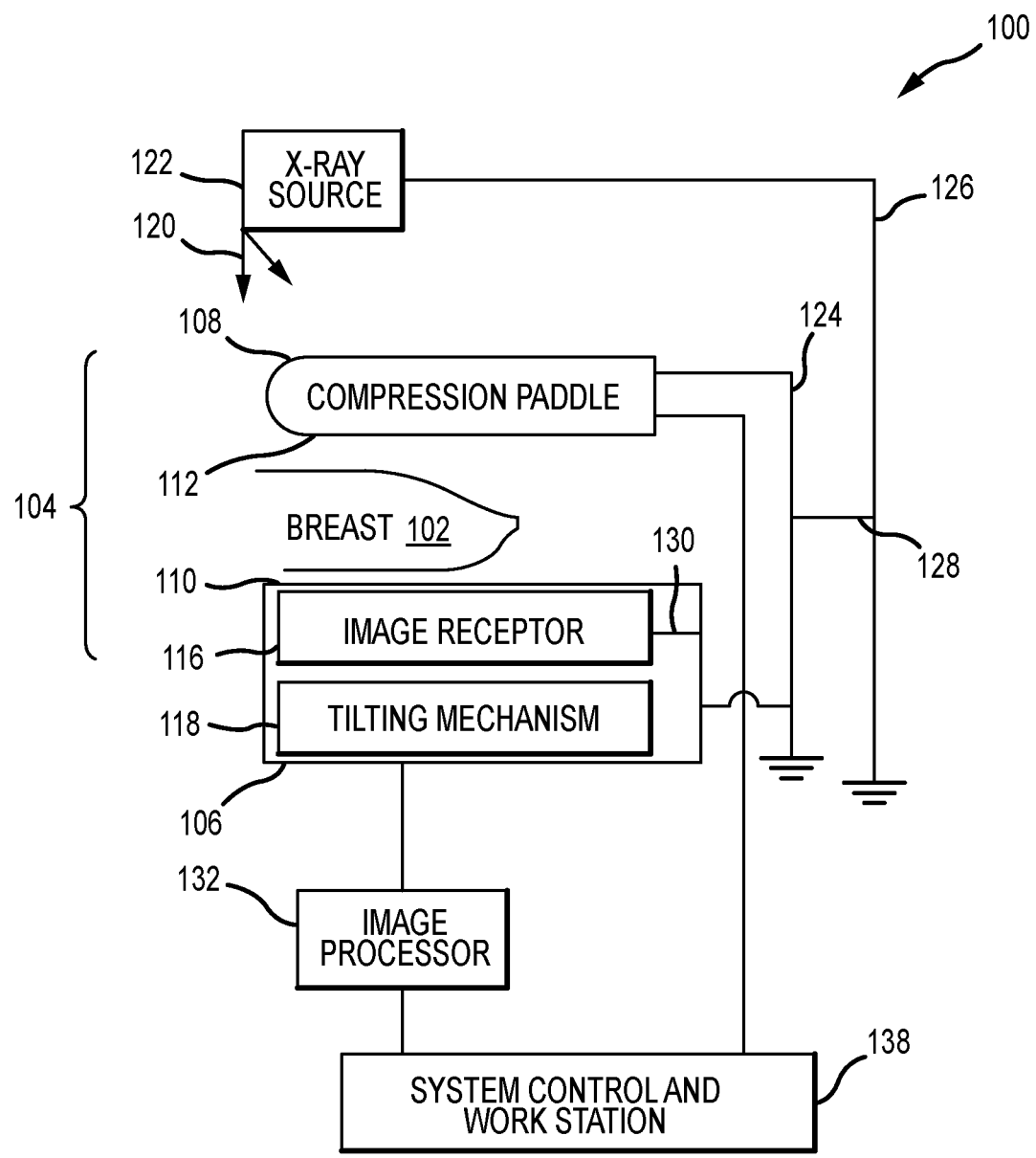
FIG. 1A is a schematic view of an exemplary imaging system.
Figure 1B:
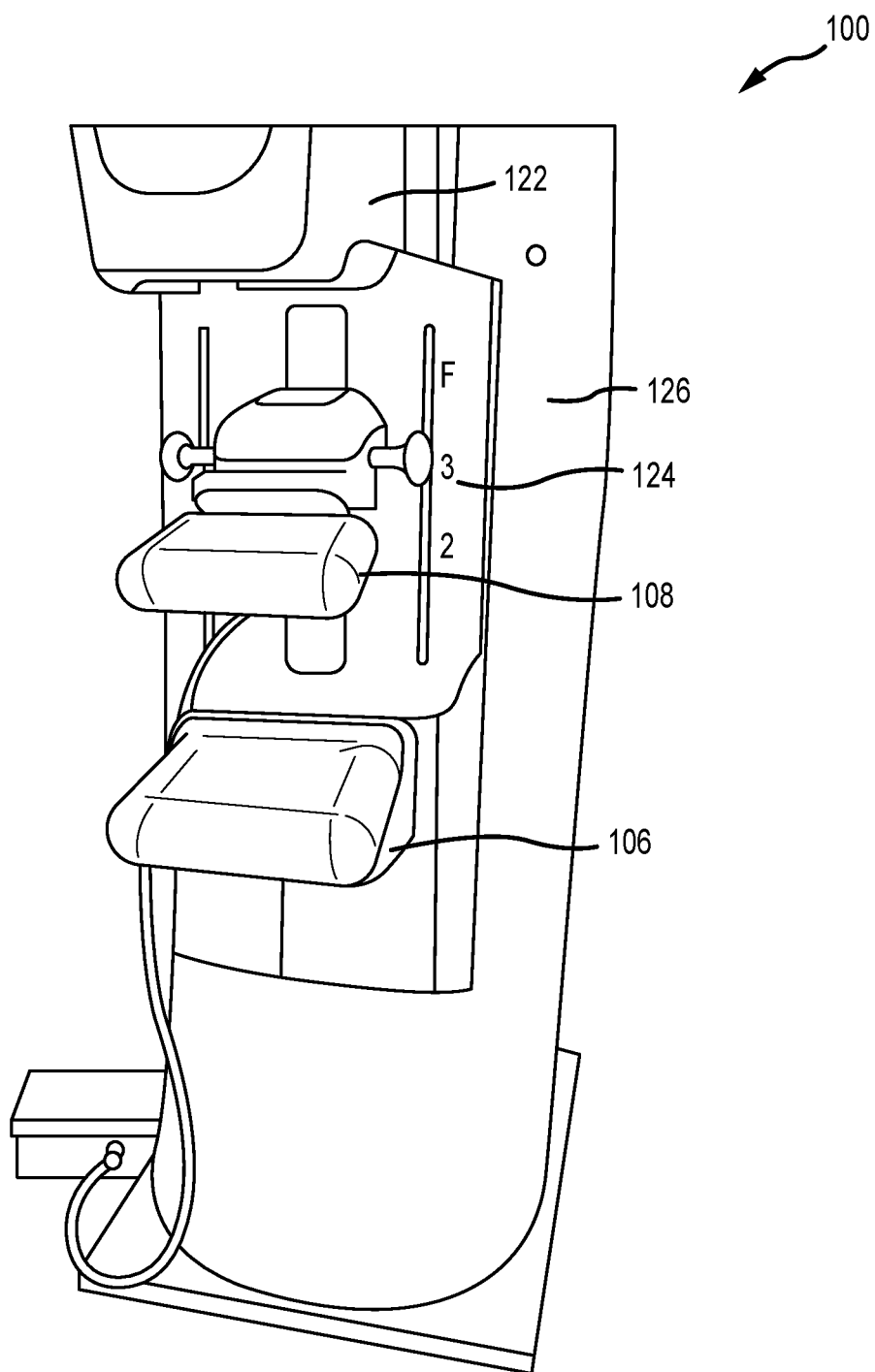
FIG. 1B is a perspective view of the imaging system of FIG. 1A.

FIG. 1A is a schematic view of an exemplary imaging system 100. FIG. 1B is a perspective view of the imaging system 100. Referring concurrently to FIGS. 1A and 1B, the imaging system 100 immobilizes a patient's breast 102 for x-ray imaging (either or both of mammography and tomosynthesis) via a breast compression immobilizer unit 104 that includes a static breast support platform 106 and a moveable compression paddle 108. The breast support platform 106 and the compression paddle 108 each have a compression surface 110 and 112, respectively, that move towards each other to compress and immobilize the breast 102. In known systems, the compression surface 110, 112 is exposed so as to directly contact the breast 102. The platform 106 also houses an image receptor 116 and, optionally, a tilting mechanism 118, and optionally an anti-scatter grid. The immobilizer unit 104 is in a path of an imaging beam 120 emanating from x-ray source 122, such that the beam 120 impinges on the image receptor 116.

The immobilizer unit 104 is supported on a first support arm 124 and the x-ray source 122 is supported on a second support arm 126. For mammography, support arms 124 and 126 can rotate as a unit about an axis 128 between different imaging orientations such as CC and MLO, so that the system 100 can take a mammogram projection image at each orientation. In operation, the image receptor 116 remains in place relative to the platform 106 while an image is taken. The immobilizer unit 104 releases the breast 102 for movement of arms 124, 126 to a different imaging orientation. For tomosynthesis, the support arm 124 stays in place, with the breast 102 immobilized and remaining in place, while at least the second support arm 126 rotates the x-ray source 122 relative to the immobilizer unit 104 and the compressed breast 102 about the axis 128. The system 100 takes plural tomosynthesis projection images of the breast 102 at respective angles of the beam 120 relative to the breast 102.

The image receptor 116 may be tilted relative to the breast support platform 106 and in sync with the rotation of the second support arm 126. The tilting can be through the same angle as the rotation of the x-ray source 122, but may also be through a different angle selected such that the beam 120 remains substantially in the same position on the image receptor 116 for each of the plural images. The tilting can be about an axis 130, which can but need not be in the image plane of the image receptor 116. The tilting mechanism 118 that is coupled to the image receptor 116 can drive the image receptor 116 in a tilting motion. For tomosynthesis imaging and/or CT imaging, the breast support platform 106 can be horizontal or can be at an angle to the horizontal, e.g., at an orientation similar to that for conventional MLO imaging in mammography. The system 100 can be solely a mammography system, a CT system, or solely a tomosynthesis system, or a "combo" system that can perform multiple forms of imaging. An example of such a combo system has been offered by the assignee hereof under the trade name Selenia Dimensions.

When the system is operated, the image receptor 116 produces imaging information in response to illumination by the imaging beam 120, and supplies it to an image processor 132 for processing and generating breast x-ray images. A system control and work station unit 138 including software controls the operation of the system and interacts with the operator to receive commands and deliver information including processed-ray images.

One challenge with the imaging system 100 is how to immobilize and compress the breast 102 for the desired or required imaging. A health professional, typically an x-ray technologist, generally adjusts the breast 102 within the immobilizer unit 104 while pulling tissue towards imaging area and moving the compression paddle 108 toward the breast support platform 106 to immobilize the breast 102 and keep it in place, with as much of the breast tissue as practicable being between the compression surfaces 110, 112.

The present technology relates to a breast compression system that moves the compression arm and compression paddle in a sequence that increases access to and visibility of the breast by the technician. Compression arm paddle movements consistent with those described herein may be particularly desirable for paddles utilizing thick foam compression elements, which often limit the visibility of and access to the breast.

The compression systems described herein may include a foam compressive element that is positioned over a compression surface and contacts the breast during compression. The foam compresses as pressure increases and is generally more comfortable than hard plastic paddles. Appropriate foam materials include super soft urethane foams, such as fire-retardant upholstery foams, that display advantageous performance characteristics. Such materials may be manufactured so as to meet the requirements of ASTM D 3574. Foams having the performance characteristics displayed in Table 1 below have displayed advantageous properties, although other foams having different performance characteristics may also be utilized.

TABLE 1

Super Soft Foam Performance Data

| Property | Test Method | Values |
| --- | --- | --- |
| Density (LB/Cubic Ft.) | ASTM D 3574 | 1.2 |
| 25% ILD (LB) | ASTM D 3574 | 12 |
| Support Factor (65%/25% Min.) | ASTM D 3574 | 1.9 |
| Air Flow (CFM) Min. | ASTM D 3574 | 3 |
| Tensile (PSI) Min. | ASTM D 3574 | 10 |
| Elongation (%) Min. | ASTM D 3574 | 200 |
| Tear (PPI) Min. | ASTM D 3574 | 1.1 |
| Resiliency (%) Min. | ASTM D 3574 | 40 |

Further testing has been performed to identify desirable foams that may be utilized as thick foam compressive elements. For example, a noise power spectrum study has been performed. In the study, a 2 inch piece of foam was compressed to various thicknesses on a Selenia Dimensions system available from the assignee hereof. Detector signals were all matched in the study and it was determined that noise changes were all due to the utilization of a foam compressive element. It was further determined that compression helps to reduce the noise generated by the foam, expect when compressed to below 2 cm thickness where further noise reduction becomes less significant. As the magnitude was increased, a spectrum shape change was also observed. Further, the noise from the foam was both high and low frequency, although low frequency noise was more enhanced in the foam images. Further results are depicted in Tables 2 and 3, below.

TABLE 2

Magnitude Study

|  | sig | nos | nos ratio |
|---|---|---|---|
| no foam | 471 | 6.31 | 1.000 |
| foam at 0 cm | 469 | 7.11 | 1.127 |
| foam at 10 cm | 470 | 6.88 | 1.090 |
| foam at 20 cm | 471 | 6.70 | 1.062 |
| foam at 34 cm | 472 | 6.54 | 1.036 |

TABLE 3

Compression Study

|  | sig | nos | nos ratio |
|---|---|---|---|
| no foam | 471 | 6.31 | 1.000 |
| foam of 5.2 cm | 472 | 7.09 | 1.123 |
| foam of 2 cm | 472 | 6.86 | 1.087 |
| foam of 1 cm | 472 | 6.81 | 1.080 |
| foam of 0.6 cm | 472 | 6.79 | 1.076 |

The foam may be secured to a hard plastic compression paddle substrate with a radiotranslucent adhesive, or may be mechanically secured thereto, for example, with hooks, straps, or other securement structures. The foam at least partially conforms in shape to the breast as the paddle is lowered and the foam compresses. This stabilizes and may entirely immobilize the breast for imaging, without requiring the compression pressure typical in breast imaging systems. Additionally, the foam may be placed on the portions of the compression paddle and breast platform that face the chest wall. As the compression paddle is lowered, the foam compresses and takes on a curved shaped that approximates the shape of the breast. However, unlike hard plastic compression paddles, compression forces need not be so high as to completely flatten the breast. Rather, the foams described herein are utilized to stabilize the breast, not necessarily to effectuate full compression, which is usually performed by flat rigid compression paddles (or by breast compression elements that have a very thin layer of foam disposed thereon.

Compression paddles are typically manufactured from a clear rigid material that enables a technician operating a breast imaging system to view the breast at various points during breast positioning and imaging. This allows the technician to properly access the breast, for example, to avoid wrinkles in the tissue, to properly position the nipple, etc. The foam compressive paddles described herein, while allowing for greater comfort for the patient, can reduce access to and visibility of the breast by the technician. Thus, the foam compressive material described herein may be lowered towards the breast in sequences of motion that allow the breast to remain visible and accessible for a significant amount of time. Additionally, although described generally in the context of compression paddles having thick foam components, the compression sequences described herein may also be leveraged in systems that utilize more traditional rigid plastic paddles, since greater breast access is possible with the compressive sequences described herein.

FIGS. 2A-2G depict partial side views of an imaging system 200 including a compression arm 202 and a compression paddle 204 at various positions during compression and imaging procedures. The imaging system 200 also includes an arm assembly 206 that is rotatable about an axis A. Other components of the imaging system 200 (e.g., the base, C-arm, etc.) are not depicted in FIGS. 2A-2G but are otherwise depicted herein, for example in FIGS. 1A and 1B. A face shield 208 is also depicted and is generally fixed to an arm assembly 206, although the connecting structure is not depicted here for clarity. The face shield 208 is generally disposed in a position substantially aligned with a front face 210 of a support platform 212. The face shield 208 prevents the x-ray source housing 209 from inadvertently contacting the patient during rotation thereof.

The compression paddle 204 depicted in FIGS. 2A-2G includes a foam compressive element 214 secured to a rigid substrate 216. As described above, the depicted compression paddle 204 may block the technician's view or hinder access if merely engaged in a horizontal orientation with the compression arm 202. As such, the compression paddle 204 is configured to pivot so as to enable better visibility of and access to positioning of the breast. More specifically, the compression paddle 204 is connected to a bracket of a strut housing 218 for removably securing the compression paddle 204 to the compression arm 202. The strut housing 218 also supports therein a motor for pivotal movement of the compression paddle 210, as well as controls and other components for extending one or more locks 219 disposed therein for locking a horizontal position of the compression paddle 204 relative to the compression arm 202. The strut housing 218 extends towards the arm assembly 206. A pair of extension arms 220 (only one of which is visible) connect the rigid substrate 216 to the strut housing 218 at a pivot mechanism 222, which may be motor driven. The pair of extension arms 220 are connected to the rigid substrate 216 proximate the lateral edges thereof, so as to form a clearance gap 224 therebetween. The clearance gap 224 is sized so as to accommodate the compression arm 202 as the compression paddle 204 pivots about the pivot mechanism 222.

Figure 2A:
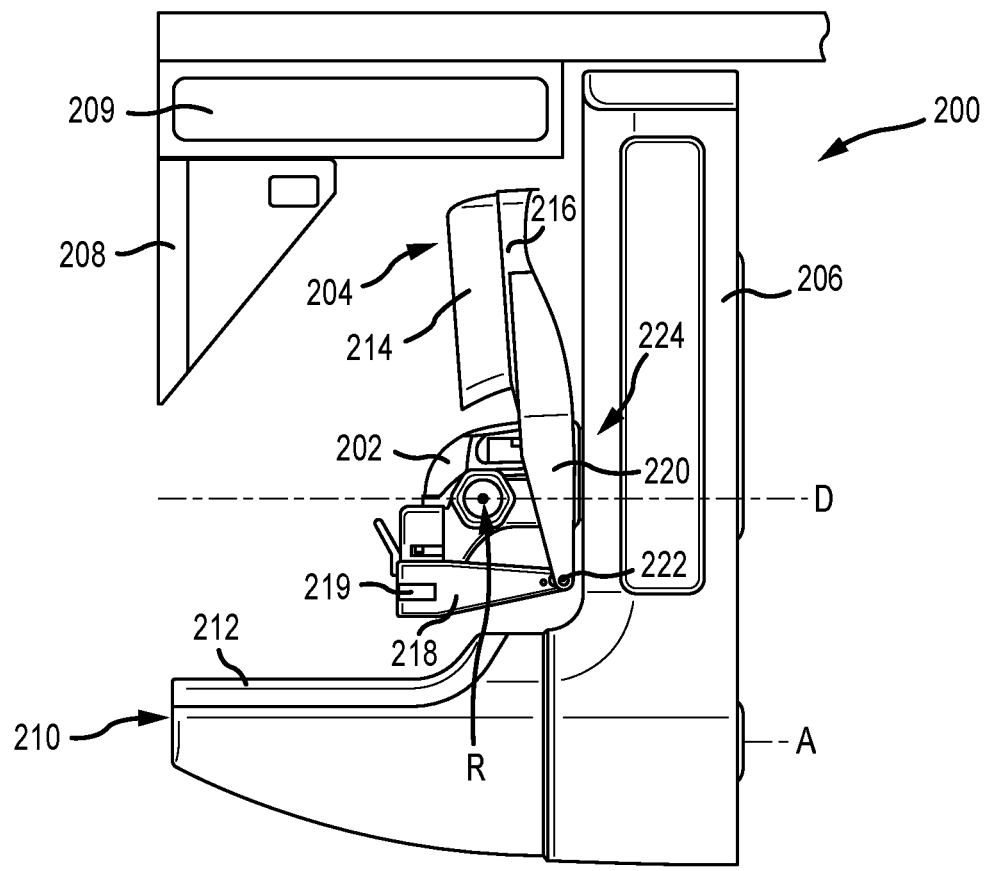
FIGS. 2A-2G depict partial side views of an imaging system including a compression arm and a compression paddle at various positions during compression procedures.
Figure 2B:
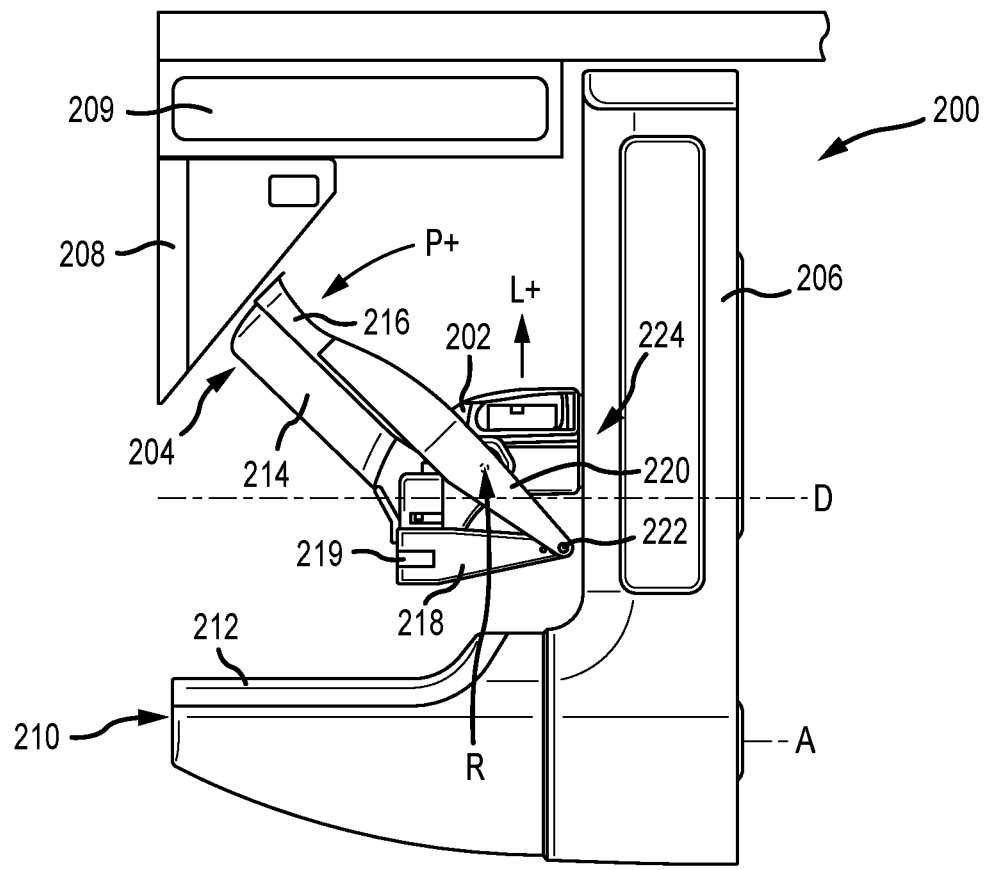
Figure 2C:
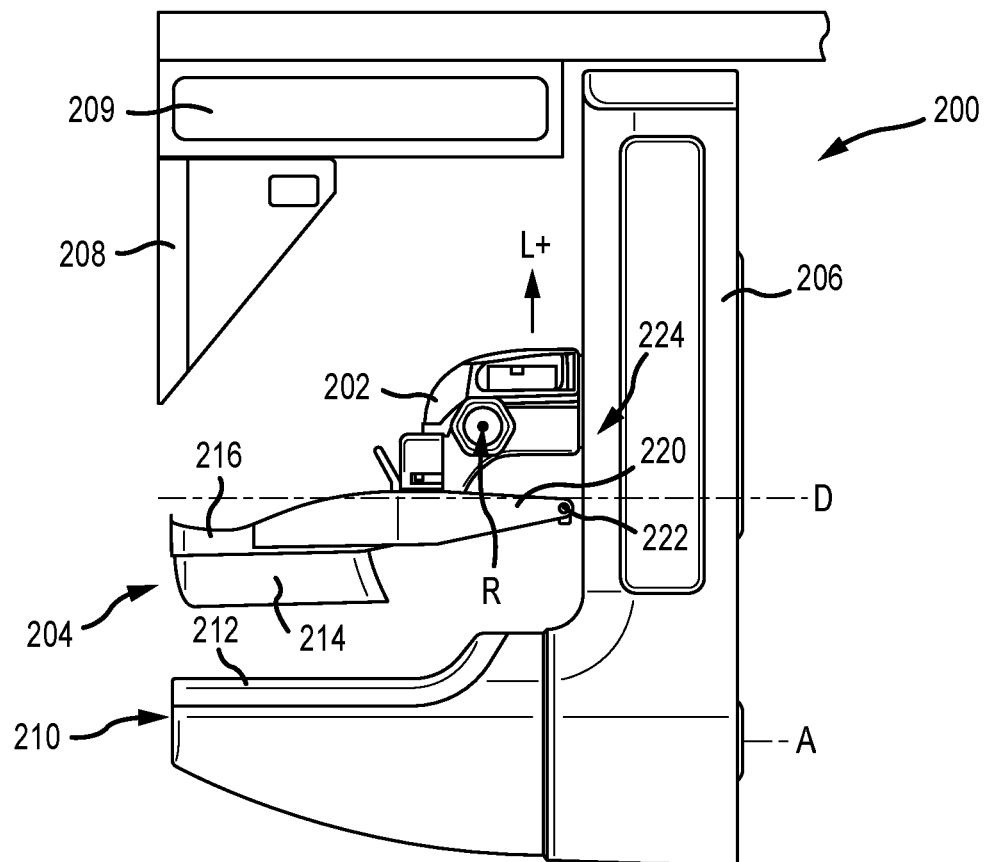
Figure 2D:
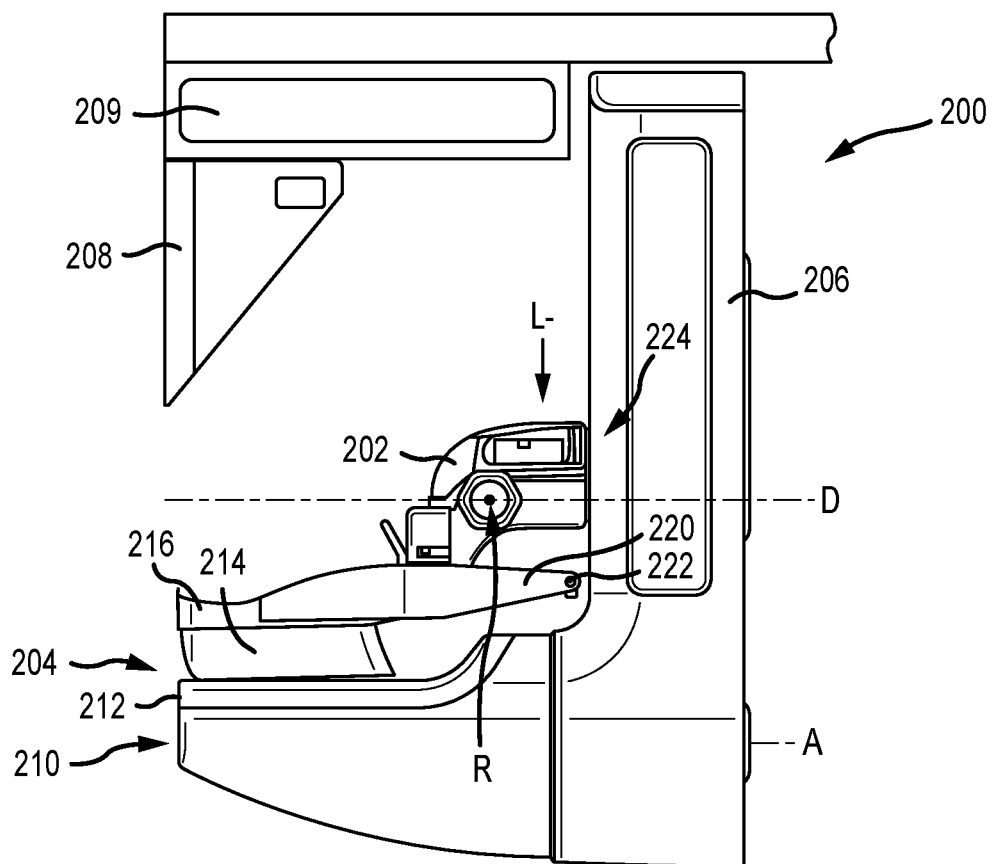
Figure 2E:
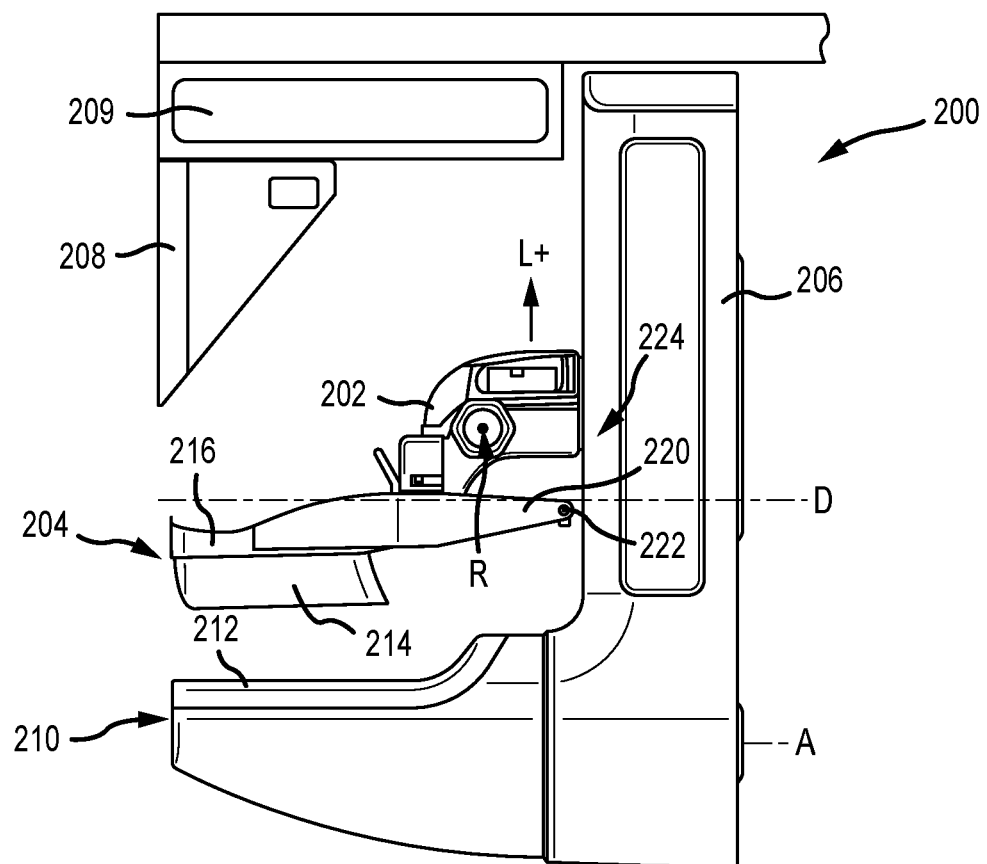
Figure 2F:
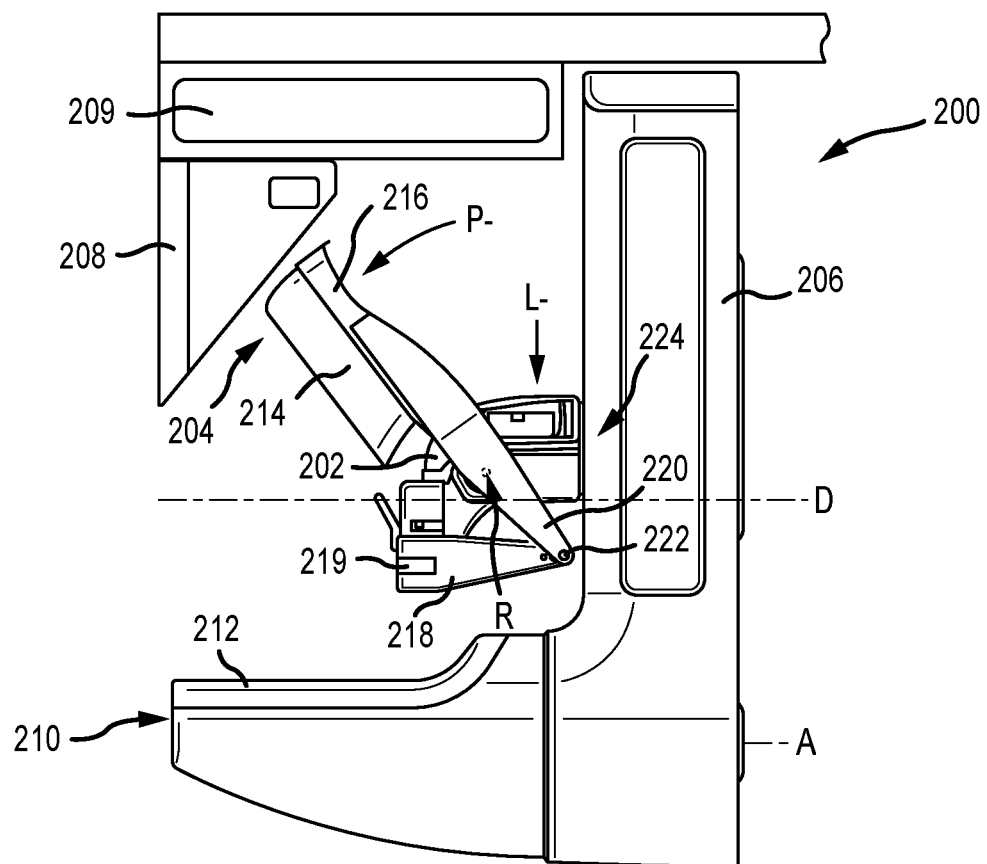
Figure 2G:
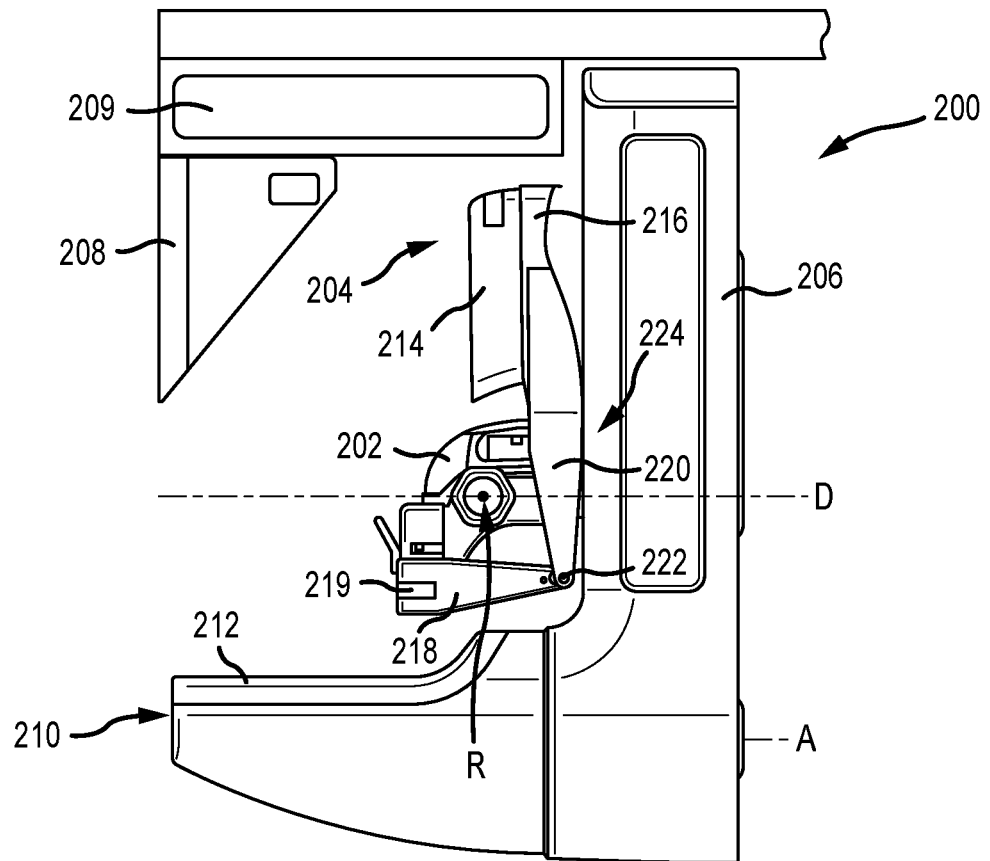

FIGS. 2A-2G also depict a datum line D, which corresponds to a distance of a reference point R on the compression arm 202 above the support platform 212 when the system 200 is in the compressed condition depicted, e.g., in FIG. 2D. In the compressed condition (which may vary from patient to patient depending on, for example, breast size, patient comfort, applied force, foam thickness, etc.), the compression paddle 204 is disposed in a horizontal orientation and at its lowest vertical position. However, it is undesirable for the compression paddle 204 to pivot directly from the substantially vertical position depicted in FIG. 2A to the compressed position of FIG. 2D. Contacting of the breast by the compression paddle 204 during pivoting movement thereof makes proper positioning of the breast difficult and may have a tendency to force a volume of the breast at of the field of view. As such, while the compression paddle pivots P+ from the substantially vertical position of FIG. 2A to a substantially horizontal position, the compression paddle moves linearly and upward (as depicted in FIGS. 2B and 2C by the change in position of the reference point R relative to the datum line D). This upward linear movement L+ occurs substantially simultaneously with the pivoting movement P+ so as to prevent the compression paddle 204 from contacting the face shield 208. Once the compression paddle 204 reaches the substantially horizontal orientation of FIG. 2C, the compression arm 202 may continue with linear upward movement L+. During the time of this movement, the locks 219 may extend from the strut housing 218 and engage the rigid substrate 216, so as to prevent pivoting movement thereof during compression. Once the compression paddle 204 is locked into place, the compression arm 202 moves linearly downward L- to the position depicted in FIG. 2D. When the compression paddle 204 is in the substantially horizontal orientation, the strut housing 218 is substantially aligned with the extension arms 220. After imaging, which is performed when the compression paddle 204 disposed as depicted in FIG. 2D, upward linear movement L+ is performed until the foam compressive element 214 is no longer engaged with the breast, as depicted in FIG. 2E. Thereafter, opposite pivotal movement P− of the compression paddle 204 along with upward linear movement L+ of the compression arm 202 is performed as depicted in FIG. 2F. At the end of these movements, the compression paddle 204 is returned to the initial substantially vertical position depicted in FIG. 2G (and FIG. 2A). In the substantially vertical orientation, the extension arms 220 are disposed at an angle (e.g., orthogonal) to the strut housing 218.

Figure 3:
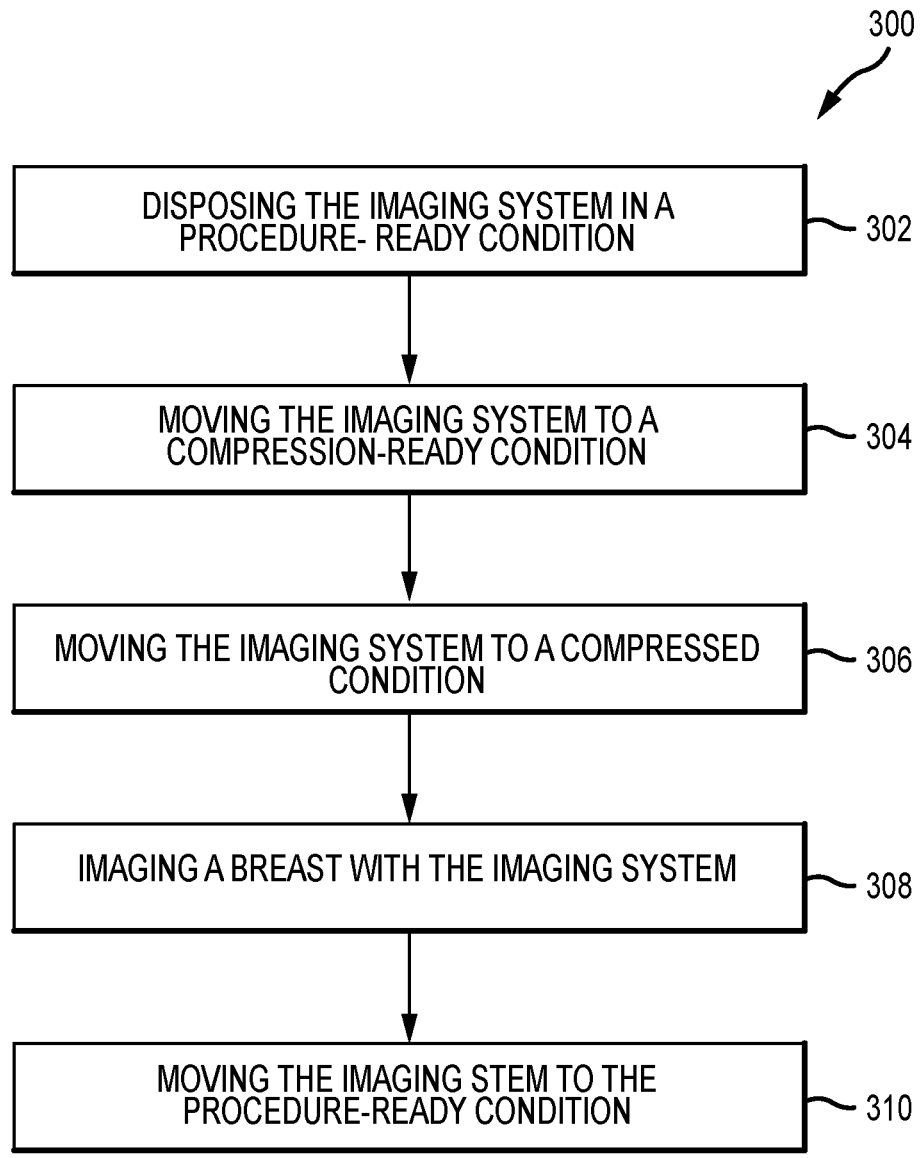
FIG. 3 depicts a method of imaging a breast with an imaging system.

Thus, the imaging system 300 of FIGS. 3A-3G may be utilized in performing a method 300 of imaging a breast, which is depicted in FIG. 3. For clarity, an imaging method 300 for CC imaging is depicted in FIGS. 3A-3G and described with regard to FIG. 3. With regard to an MLO imaging procedure, appropriate orientation, positioning, and movement of the various imaging system components will be apparent to a person of skill in the art. The method 300 is performed on a breast imaging system that performs x-ray imaging, such as mammographic imaging, tomosynthesis imaging, or both types of imaging. Examples of such systems are depicted and described herein. In operation 302, the method 300 includes disposing the imaging system in a procedure-ready position. The procedure-ready condition contemplates a condition of the imaging system when a breast is first placed in contact with the breast support. Further, in the procedure-ready condition, the face shield may be positioned so as to prevent contact between the patient and the movable x-ray source housing. Additionally, the tube head may be oriented so as to enable access to the breast by the technician; this orientation may vary depending on the type of imaging being performed (e.g., CC or MLO), technician preferences, patient comfort, etc. The compression paddle may be in an orientation substantially orthogonal to, and disposed at a first height above, the support platform. Thus, a procedure-ready condition for CC imaging is depicted in FIG. 3A. In this condition, the breast is accessible for positioning and manipulation by the technician. In operation 304, the method 300 includes moving the imaging system to a compression-ready condition. The compression-ready condition contemplates a condition where compression of the breast may begin to be performed, and may include any one or more of the following conditions. For example, the compression paddle may be oriented in a substantially horizontal orientation and the compression arm may be disposed at a second height above the support platform. Typically, at this second height, there is minimal or no contact between the foam compressive element and the breast, such that technician manipulation of the breast is still possible. Such a compression-ready condition is depicted in FIG. 3C. The compression-ready condition is reached, in an example, by substantially simultaneously pivoting the compression paddle while linearly moving the compression arm. This simultaneous movement is depicted, for example, in FIG. 3B, where the compression arm moves linearly upward, such that the second height (once reached as part of reaching the compression-ready condition) is greater than the first height.

In operation 306, the method 300 includes moving the imaging system to a compressed condition. The compressed condition contemplates a condition where compression of the breast is complete and the breast is ready for imaging. The compressed condition may include any one or more of the following conditions. For example, the compression paddle may be in a substantially horizontal orientation (although the compression may cause some slight deformation or deflection of the substrate of the compression paddle) and the compression arm is disposed at a third height above the compression platform. This third height may depend on a number of factors such as applied force, breast size, foam thickness, etc. In examples, the third height may be less than the first height, described above. This condition is depicted in FIG. 3D. In general, only linear movement of the compression arm between the compression-ready condition of FIG. 3C and the compressed condition of FIG. 3D is performed. In operation 308, the method 300 includes imaging the breast, which is performed when the imaging system is in the compressed condition.

After imaging of the breast in operation 308, the method continues to operation 310, which includes moving the imaging system to the procedure-ready condition, as depicted in FIG. 3G (and FIG. 3A). To move from the procedure-ready condition, reverse movements of the compression paddle and compression arm are performed. For example, the compression arm may first move linearly upward (e.g., to the condition depicted in FIG. 3E) so as to uncompress the breast. Thereafter, clockwise pivoting movement of the compression paddle may occur substantially simultaneously with downward linear movement of the compression arm (as depicted in FIG. 3F). This substantially simultaneous movement helps prevent the compression paddle from contacting the face shield. The procedure-ready condition of FIG. 3G is reached when the compression paddle reaches a substantially vertical orientation and the compression paddle is disposed once again at the first height. In other examples, however, the compression arm or paddle may return to a different position, away from the patient, but not necessarily providing complete breast visibility and access by the technician, since such access is not necessarily required once the imaging procedure is concluded.

Figure 4A:
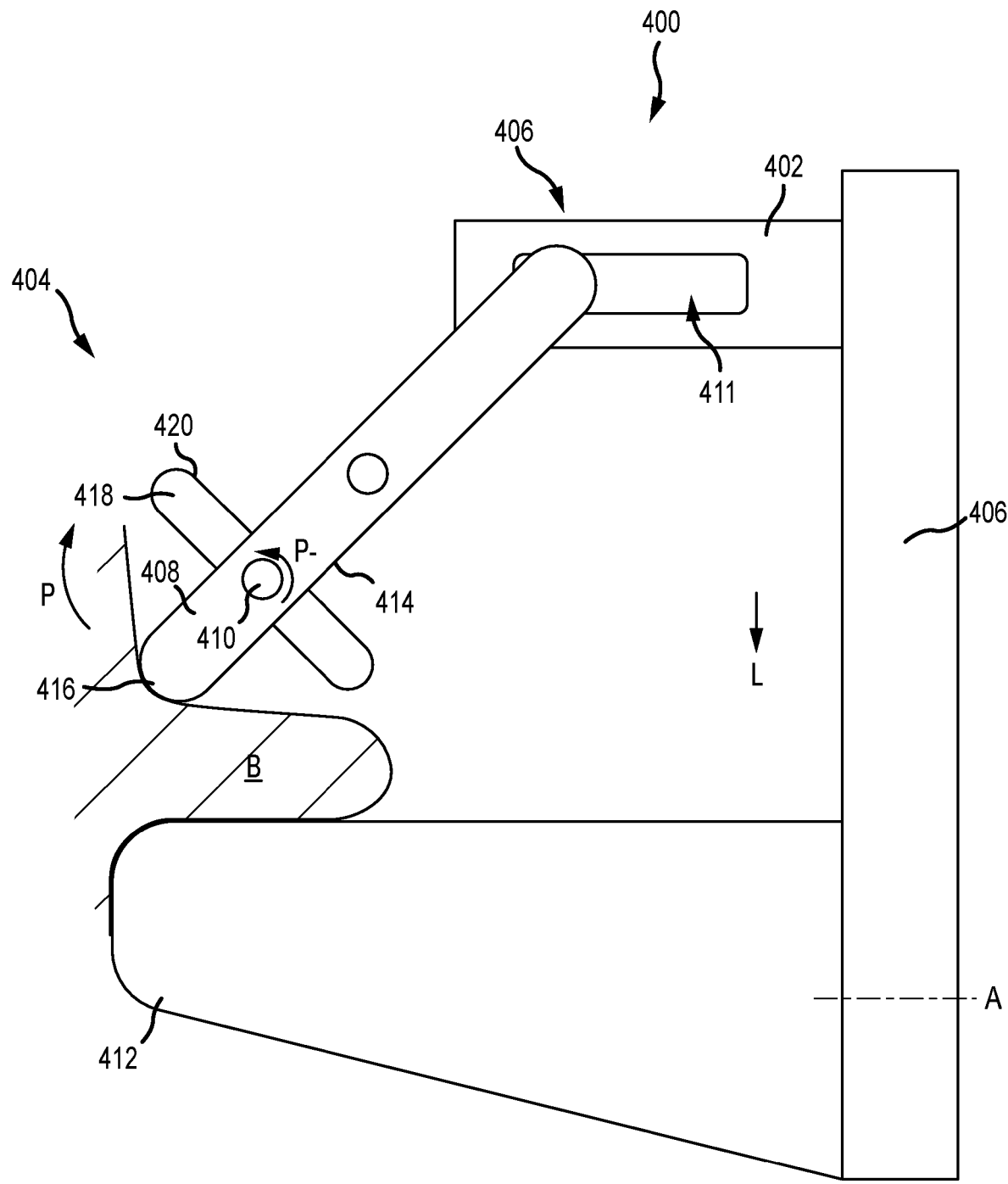
FIGS. 4A-4B partial depict side views of an imaging system including a compression arm and a compression paddle at various positions during compression procedures.
Figure 4B:
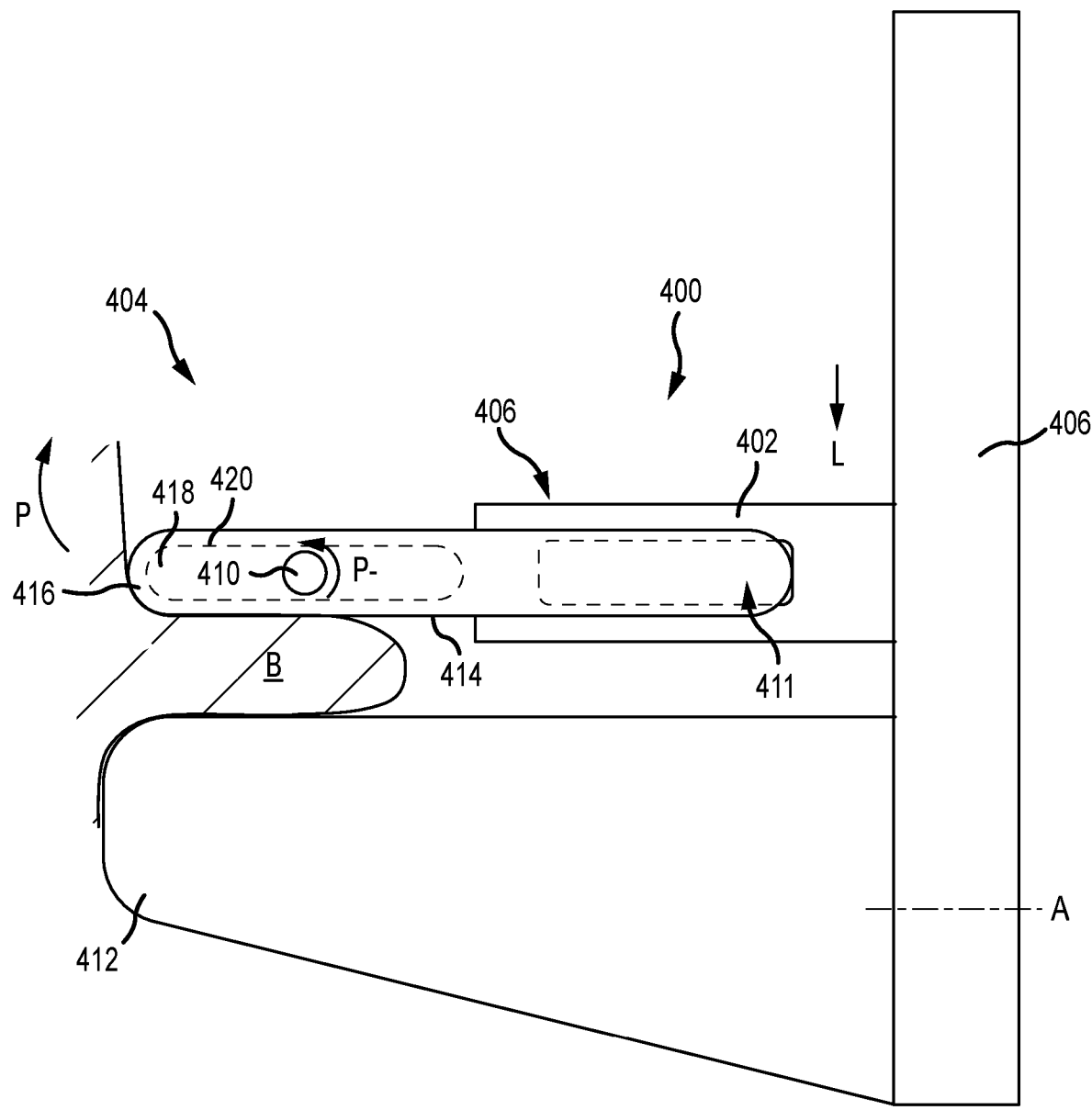

FIGS. 4A-4B partial depict side views of an imaging system 400 including a compression arm 402 and a compression paddle 404 at various positions during compression and imaging procedures. The imaging system 400 also includes an arm assembly 406 that is rotatable about an axis A. Other components of the imaging system 400 (e.g., the base, C-arm, etc.) are not depicted in FIGS. 4A-4B but are otherwise depicted herein, for example in FIGS. 1A and 1B. A support platform 412 is used to support a breast B from below. The compression paddle 404, in this case, includes a rigid frame 409 that is pivotably and slidably connected to the compression arm 402 at an interface mechanism 408. The interface mechanism 408 includes a pivotable connector 410 secured to the frame 409. Further, this pivotable connector 410 is slidably engaged with the compression arm 402 at a slide mechanism, disposed in a slot 411. The frame 409, includes two side walls 414 and a leading wall 416 spanning the ends thereof. The leading wall 416 may be at least partially curved so as to more comfortably contact the breast B. A foam compressive element 418 is secured to a rigid substrate 420 that is pivotably secured to the side walls 414 at a pivot 422, which is disposed proximate a mid-point of the frame 408 and substrate 420.

At the beginning of an imaging procedure using the imaging system 400 partially depicted in FIGS. 4A and 4B, a breast B is first placed on the breast support platform 412. Further, the foam compressive element 418 is disposed in the non-contacting position depicted in FIG. 4A, where no part of the breast B is in contact with the foam compressive element 418. The compression arm 402 is lowered until the leading wall 416 contacts the breast B. As this downward linear movement L– of the compression arm 402 continues, the frame 414 pivots P until the foam compressive element 418 contacts the breast B. During this pivoting P, the pivotable connector 410 slides S within the slot 411, away from the breast B. Pivoting P of the frame 414 (and sliding of the pivot mechanism 410) continues, and is now accompanied by an opposite pivoting P– movement of the foam compressive element 418 and substrate 420, until maximum compression is reached. In this condition, the frame 414 and foam compressive element 418 may be substantially aligned, as depicted in FIG. 4B, although this is not required.

Figure 5:
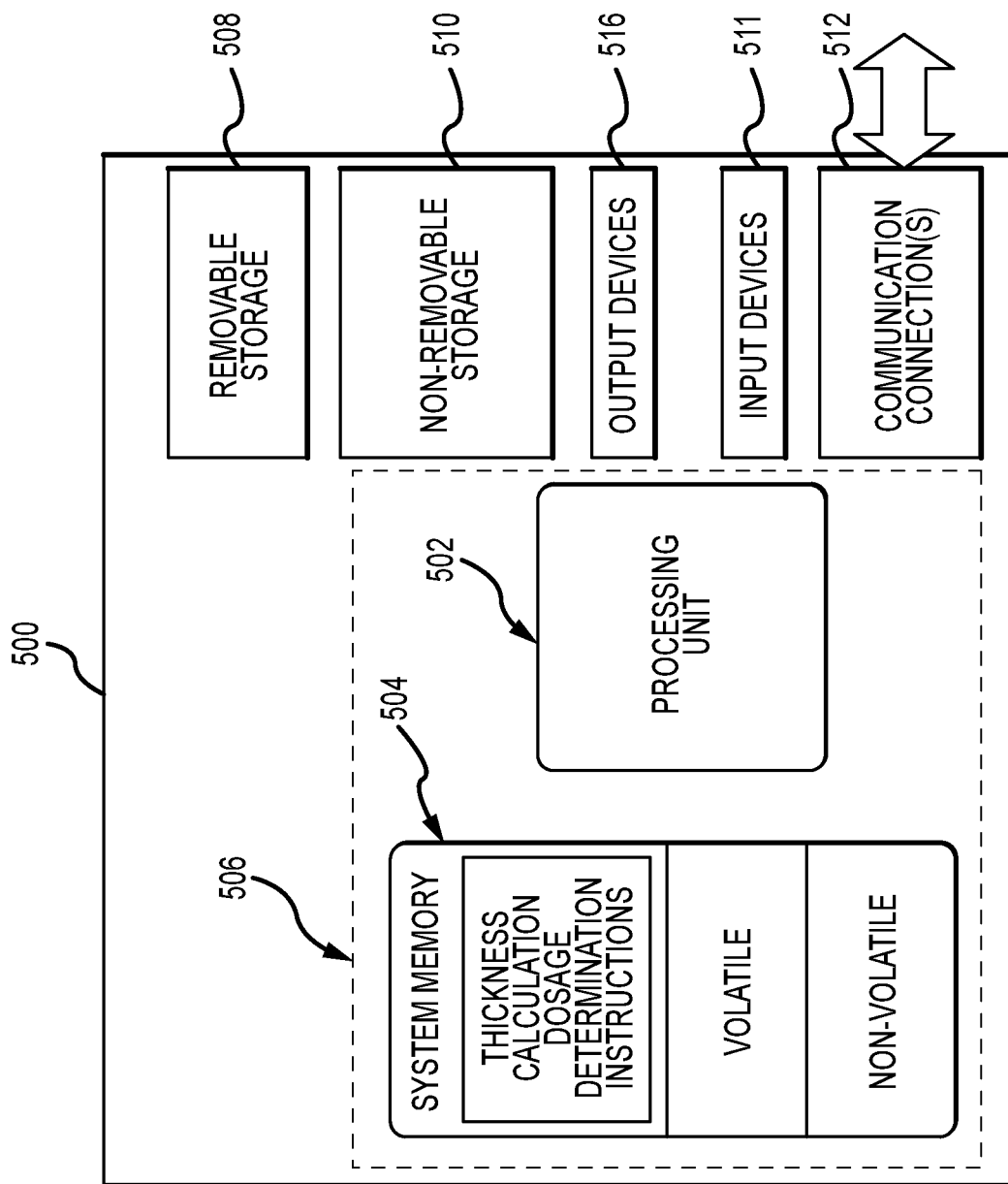
FIG. 5 depicts an example of a suitable operating environment in which one or more of the present examples can be implemented.

FIG. 5 illustrates one example of a suitable operating environment 500 in which one or more of the present examples can be implemented. This operating environment may be incorporated directly into the imaging systems disclosed herein, or may be incorporated into a computer system discrete from, but used to control, a the imaging and compression systems described herein. This is only one example of a suitable operating environment and is not intended to suggest any limitation as to the scope of use or functionality. Other well-known computing systems, environments, and/or configurations that can be suitable for use include, but are not limited to, imaging systems, personal computers, server computers, hand-held or laptop devices, multiprocessor systems, microprocessor-based systems, programmable consumer electronics such as smart phones, network PCs, minicomputers, mainframe computers, tablets, distributed computing environments that include any of the above systems or devices, and the like.

In its most basic configuration, operating environment 500 typically includes at least one processing unit 502 and memory 504. Depending on the exact configuration and type of computing device, memory 504 (storing, among other things, instructions to pivot the compression paddle, raise and lower the compression arm, or perform other methods disclosed herein) can be volatile (such as RAM), non-volatile (such as ROM, flash memory, etc.), or some combination of the two. This most basic configuration is illustrated in FIG. 11 by dashed line 506. Further, environment 500 can also include storage devices (removable, 508, and/or non-removable, 510) including, but not limited to, magnetic or optical disks or tape. Similarly, environment 500 can also have input device(s) 514 such as touch screens, keyboard, mouse, pen, voice input, etc., and/or output device (s) 516 such as a display, speakers, printer, etc. Also included in the environment can be one or more communication connections 512, such as LAN, WAN, point to point, Bluetooth, RF, etc.

Operating environment 500 typically includes at least some form of computer readable media. Computer readable media can be any available media that can be accessed by processing unit 502 or other devices having the operating environment. By way of example, and not limitation, computer readable media can include computer storage media and communication media. Computer storage media includes volatile and nonvolatile, removable and non-removable media implemented in any method or technology for storage of information such as computer readable instructions, data structures, program modules or other data. Computer storage media includes, RAM, ROM, EEPROM, flash memory or other memory technology, CD-ROM, digital versatile disks (DVD) or other optical storage, magnetic cassettes, magnetic tape, magnetic disk storage or other magnetic storage devices, solid state storage, or any other tangible medium which can be used to store the desired information. Communication media embodies computer readable instructions, data structures, program modules, or other data in a modulated data signal such as a carrier wave or other transport mechanism and includes any information delivery media. The term "modulated data signal" means a signal that has one or more of its characteristics set or changed in such a manner as to encode information in the signal. By way of example, and not limitation, communication media includes wired media such as a wired network or direct-wired connection, and wireless media such as acoustic, RF, infrared and other wireless media. Combinations of the any of the above should also be included within the scope of computer readable media. A computer-readable device is a hardware device incorporating computer storage media.

The operating environment 500 can be a single computer operating in a networked environment using logical connections to one or more remote computers. The remote computer can be a personal computer, a server, a router, a network PC, a peer device or other common network node, and typically includes many or all of the elements described above as well as others not so mentioned. The logical connections can include any method supported by available communications media. Such networking environments are commonplace in offices, enterprise-wide computer networks, intranets and the Internet.

In some embodiments, the components described herein include such modules or instructions executable by computer system 500 that can be stored on computer storage medium and other tangible mediums and transmitted in communication media. Computer storage media includes volatile and non-volatile, removable and non-removable media implemented in any method or technology for storage of information such as computer readable instructions, data structures, program modules, or other data. Combinations of any of the above should also be included within the scope of readable media. In some embodiments, computer system 500 is part of a network that stores data in remote storage media for use by the computer system 500.

Figure 6:
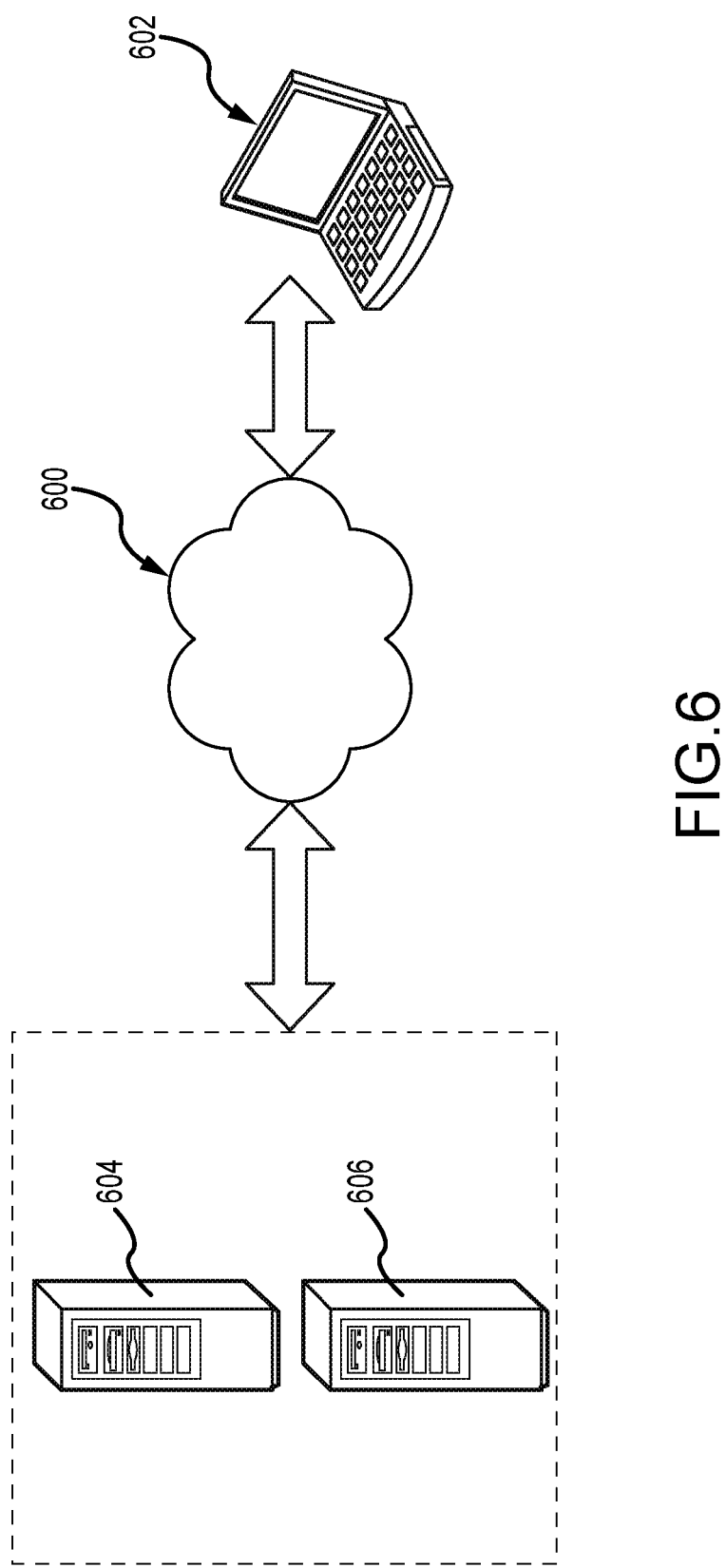
FIG. 6 depicts an example of a network in which the various systems and methods disclosed herein may operate.

FIG. 6 is an embodiment of a network 600 in which the various systems and methods disclosed herein may operate. In embodiments, a client device, such as client device 602, may communicate with one or more servers, such as servers 604 and 606, via a network 608. In embodiments, a client device may be a standalone imaging system (e.g., imaging system 120 depicted in FIG. 1A) that includes all the functionality described herein. The client device may also include or incorporate a laptop, a personal computer, a smart phone, a PDA, a netbook, or any other type of computing device, such as the computing device in FIG. 5. In examples, such a client device may be connected to an imaging system. In embodiments, servers 604 and 606 may also be any type of computing device, such as the computing device illustrated in FIG. 5. Network 608 may be any type of network capable of facilitating communications between the client device and one or more servers 604 and 606. For example, the surface image data and the internal image data may be acquired locally via the imaging systems and communicated to another computing device(s) for further processing, such as an image acquisition workstation or a cloud-based service. Examples of such networks include, but are not limited to, LANs, WANs, cellular networks, and/or the Internet.

In embodiments, the various systems and methods disclosed herein may be performed by one or more server devices. For example, in one embodiment, a single server, such as server 604 may be employed to perform the systems and methods disclosed herein, such as the methods for imaging discussed herein. Client device 602 may interact with server 604 via network 608. In further embodiments, the client device 602 may also perform functionality disclosed herein, such as scanning and image processing, which can then be provided to servers 604 and/or 606.

This disclosure described some examples of the present technology with reference to the accompanying drawings, in which only some of the possible examples were shown. Other aspects can, however, be embodied in many different forms and should not be construed as limited to the examples set forth herein. Rather, these examples were provided so that this disclosure was thorough and complete and fully conveyed the scope of the possible examples to those skilled in the art.

Although specific examples were described herein, the scope of the technology is not limited to those specific examples. One skilled in the art will recognize other examples or improvements that are within the scope of the present technology. Therefore, the specific structure, acts, or media are disclosed only as illustrative examples. Examples according to the technology may also combine elements or components of those that are disclosed in general but not expressly exemplified in combination, unless otherwise stated herein. The scope of the technology is defined by the following claims and any equivalents therein.

What is claimed is:

1. An imaging system for imaging a breast, the system comprising:
    an x-ray source housing configured to rotate relative the breast;
    an x-ray source disposed within the x-ray source housing;
    an arm assembly rotatable independent of the x-ray source housing;
    an x-ray receptor housing extending from the arm assembly, wherein the x-ray receptor housing comprises a breast support platform;
    an x-ray receptor disposed within the x-ray receptor housing;
    a compression arm assembly movably connected to the arm assembly substantially between the x-ray source housing and the x-ray receptor housing, wherein the compression arm assembly is movable between a first linear position proximate the x-ray receptor housing and a second linear position distal the x-ray receptor housing;
    a compression paddle comprising:
        a strut for removably securing the compression paddle to the compression arm assembly;
        a substrate; and
        a pair of extension arms extending from the substrate, wherein the pair of extension arms are pivotably connected to the strut between a first pivoted position where the pair of extension arms are substantially aligned with the strut and a second pivoted position where the pair of extension arms are disposed at an angle to the strut.

2. The imaging system of claim 1, wherein the pair of extension arms define therebetween a clearance gap, and wherein when in the first pivoted position, the strut is disposed in the clearance gap, and wherein when in the second pivoted position, the compression arm assembly is disposed in the clearance gap.

3. The imaging system of claim 1, wherein the angle comprises a substantially orthogonal angle.

4. The imaging system of claim 1, further comprising a foam secured to the substrate.

5. The imaging system of claim 1, further comprising at least one system control for controlling a pivoting movement of the compression paddle and a linear movement of the compression arm assembly.

6. A method of imaging a breast with an imaging system comprising a support platform disposed in a substantially horizontal orientation, a compression arm linearly positionable relative to the support platform, and a compression paddle pivotably positionable relative to the compression arm, the method comprising:
    disposing the imaging system in a procedure-ready condition, wherein in the procedure-ready condition, the compression paddle in is a substantially vertical orientation and the compression arm is disposed at a first height above the support platform;
    moving the imaging system to a compression-ready condition, wherein in the compression-ready condition, the compression paddle in is a substantially horizontal orientation and the compression arm is disposed at a second height above the support platform, wherein the second height is greater than the first height; and
    moving the imaging system to a compressed condition, wherein in the compressed condition, the compression paddle in is a substantially horizontal orientation and the compression arm is disposed at a third height above the support platform.

7. The method of claim 6, wherein the third height is less than the first height.

8. The method of claim 6, wherein during movement to the compression-ready condition, a pivotal movement of the compression paddle is performed substantially simultaneously with a linear movement of the compression arm.

9. The method of claim 6, wherein during movement to the compressed condition, only linear movement of the compression arm is performed.

10. The method of claim 6, further comprising imaging the breast when the imaging system is in the compressed condition.

11. The method of claim 8, wherein the linear movement of the compression arm comprises an upward linear movement of the compression arm.

12. The method of claim 8, wherein the substantially simultaneous pivotal movement of the compression arm and linear movement of the compression arm prevents contact between the compression paddle and a face shield of the imaging system.

13. The method of claim 6, further comprising locking the compression paddle in the compression-ready condition.

14. The method of claim 13, wherein the compression paddle is connected to the compression arm via a strut.

15. The method of claim 14, wherein locking the compression paddle comprises extending a lock from the strut to engage at least a portion of the compression paddle.

16. The imaging system of claim 1, wherein the strut comprises a lock selectively engageable with at least a portion of the compression paddle.

17. The imaging system of claim 16, wherein the lock is engageable with the compression paddle when the pair of extension arms are in the first pivoted position.

18. The imaging system of claim 2, wherein the compression arm assembly is disposed in the clearance gap.

19. The imaging system of claim 4, wherein the foam comprises a thick foam.

20. The imaging system of claim 19, wherein the thick foam has a thickness of about 2 inches.

* * * * *